(12) United States Patent
Vad

(10) Patent No.: US 10,149,777 B2
(45) Date of Patent: Dec. 11, 2018

(54) ORIENTATION MARKER ON PUSHER FOR DEPLOYMENT OF ENDOLUMINAL PROSTHESES

(71) Applicant: COOK MEDICAL TECHNOLOGIES LLC, Bloomington, IN (US)

(72) Inventor: Siddharth Vad, Irvine, CA (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 207 days.

(21) Appl. No.: 14/965,104

(22) Filed: Dec. 10, 2015

(65) Prior Publication Data

US 2016/0175131 A1 Jun. 23, 2016

Related U.S. Application Data

(60) Provisional application No. 62/093,718, filed on Dec. 18, 2014.

(51) Int. Cl.
| | |
|---|---|
| *A61F 2/954* | (2013.01) |
| *A61F 2/962* | (2013.01) |
| *A61F 2/966* | (2013.01) |
| *A61M 25/01* | (2006.01) |
| *A61F 2/06* | (2013.01) |

(52) U.S. Cl.
CPC ............ *A61F 2/962* (2013.01); *A61F 2/966* (2013.01); *A61M 25/0108* (2013.01); *A61F 2002/065* (2013.01); *A61F 2002/9665* (2013.01); *A61F 2250/0098* (2013.01)

(58) Field of Classification Search
CPC .. A61F 2/962; A61F 2/966; A61F 2250/0098; A61F 2002/065; A61F 2002/9665
See application file for complete search history.

(56) References Cited

U.S. PATENT DOCUMENTS

| | | | | |
|---|---|---|---|---|
| 4,938,220 A | * | 7/1990 | Mueller, Jr. | A61B 6/12 600/435 |
| 5,203,777 A | * | 4/1993 | Lee | A61M 25/0108 600/435 |
| 5,609,627 A | * | 3/1997 | Goicoechea | A61F 2/07 128/898 |

(Continued)

FOREIGN PATENT DOCUMENTS

| | | |
|---|---|---|
| WO | WO00/071059 | 11/2000 |
| WO | WO02/083038 | 10/2002 |

OTHER PUBLICATIONS

Examination Report for EP 15275263.0 dated Oct. 4, 2017, 6 pgs.

(Continued)

*Primary Examiner* — Julian W Woo
(74) *Attorney, Agent, or Firm* — Brinks Gilson & Lione

(57) ABSTRACT

The present embodiments provide system and methods for deploying an endoluminal prosthesis. In one example, the system comprises a sheath, and a stent-graft disposed within the sheath in a delivery state. A pusher having proximal and distal sections is disposed at least partially within the sheath in the delivery state. An orientation marker is disposed on the pusher. The orientation marker extends less than 360 degrees around a circumference of the pusher.

9 Claims, 2 Drawing Sheets

(56) References Cited

U.S. PATENT DOCUMENTS

| | | | |
|---|---|---|---|
| 6,520,934 B1* | 2/2003 | Lee | A61M 25/0108 604/103.1 |
| 7,763,063 B2* | 7/2010 | Arbefeuille | A61F 2/07 623/1.11 |
| 8,167,930 B2* | 5/2012 | Allen | A61F 2/06 623/1.24 |
| 8,535,370 B1* | 9/2013 | Eckert | A61F 2/07 623/1.13 |
| 9,675,456 B2* | 6/2017 | Quill | A61F 2/2436 |
| 9,974,675 B2* | 5/2018 | Beard | A61F 2/07 |
| 2004/0267348 A1 | 12/2004 | Gunderson et al. | |
| 2009/0163708 A1 | 6/2009 | Tieu | |
| 2013/0073032 A1 | 3/2013 | Wang | |
| 2013/0338752 A1 | 12/2013 | Geusen et al. | |
| 2014/0180387 A1 | 6/2014 | Khenansho et al. | |
| 2014/0277340 A1 | 9/2014 | White et al. | |
| 2014/0277355 A1 | 9/2014 | Roeder | |

OTHER PUBLICATIONS

Extended European Search Report for EP15275263 dated May 24, 2016, 8 pgs.
Office Action in European Application No. 15275263.0, dated Aug. 17, 2018, pp. 1-6.

\* cited by examiner

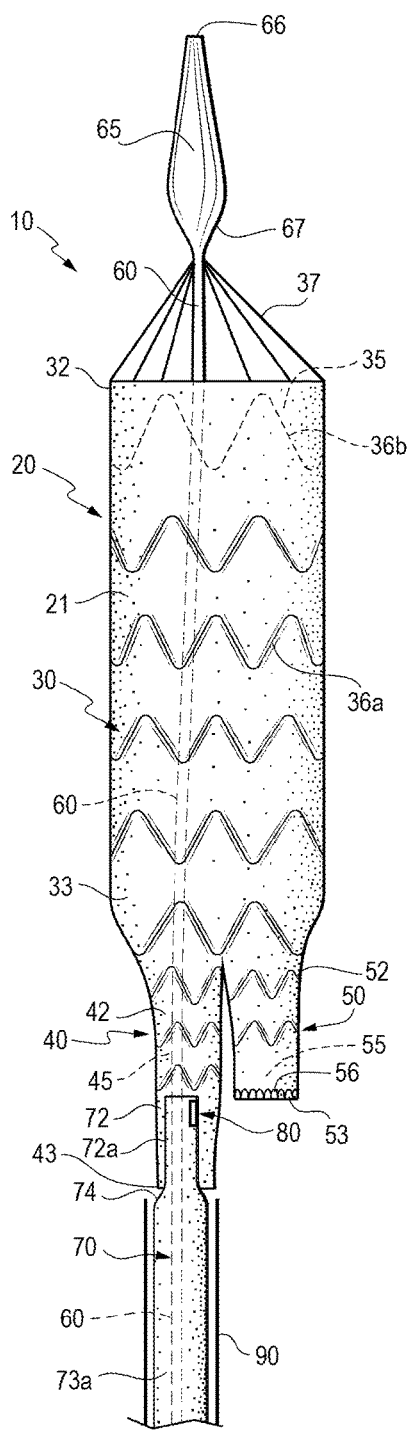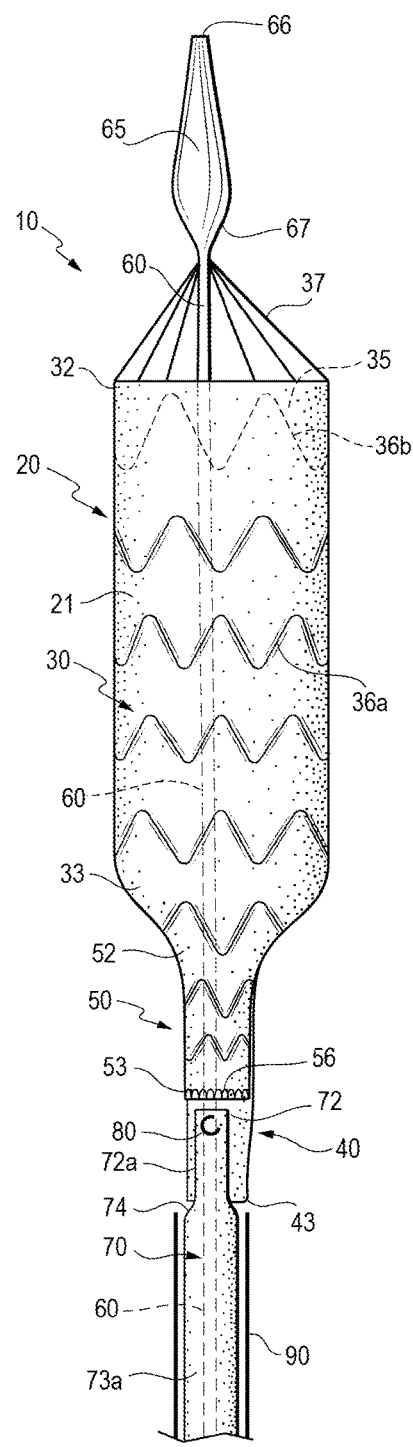

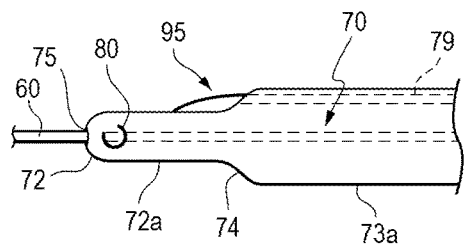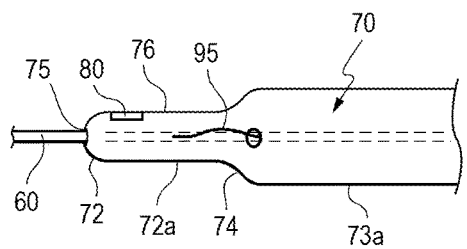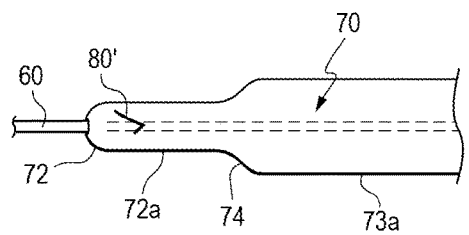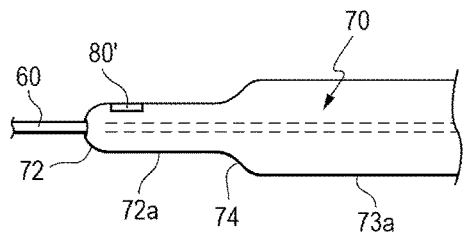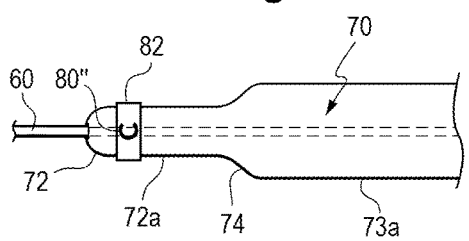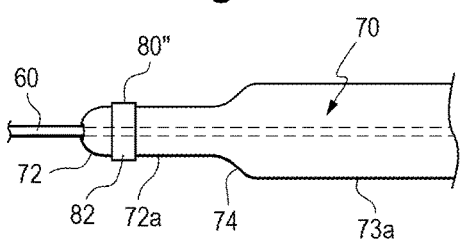

ORIENTATION MARKER ON PUSHER FOR DEPLOYMENT OF ENDOLUMINAL PROSTHESES

PRIORITY CLAIM

This invention claims the benefit of priority of U.S. Provisional Application Ser. No. 62/093,718, entitled "Orientation Marker on Pusher for Deployment of Endoluminal Prostheses," filed Dec. 18, 2014, the disclosure of which is hereby incorporated by reference in its entirety.

BACKGROUND

The present embodiments relate generally to medical devices, and more particularly, to an orientation marker used to assist in deployment of endoluminal prostheses.

The functional vessels of human and animal bodies, such as blood vessels and ducts, occasionally weaken or even rupture. For example, the aortic wall can weaken, resulting in an aneurysm. Upon further exposure to hemodynamic forces, such an aneurysm can rupture. One study found that in Western European and Australian men who are between 60 and 75 years of age, aortic aneurysms greater than 29 mm in diameter are found in 6.9% of the population, and those greater than 40 mm are present in 1.8% of the population.

One surgical intervention for weakened, aneurysmal, or ruptured vessels involves the use of an endoluminal prosthesis such as a stent-graft. Such a prosthesis may provide some or all of the functionality of the original, healthy vessel and/or preserve any remaining vascular integrity by replacing a length of the existing vessel wall that spans the site of vessel failure. It is preferable for the prosthesis to seal off the failed portion of the vessel. For weakened or aneurysmal vessels, even a small leak in the prosthesis may lead to the pressurization of or flow in the treated vessel which may aggravate the condition that the prosthesis was intended to treat. A prosthesis of this type can treat, for example, aneurysms of the abdominal aortic, iliac, or renal arteries.

In general, delivery and deployment devices for endoluminal prostheses may include devices for retaining and releasing the prosthesis into the body lumen. For example, such a device may include a sheath for radially retaining the prosthesis in a compressed configuration. A pusher may be provided for pushing the sheath and the prosthesis into the body lumen and for delivering the device into a desired position. To deploy the prosthesis, the sheath may be withdrawn over the pusher and the prosthesis, thereby causing the prosthesis to become exposed and to expand into the body lumen.

Some existing endoluminal prostheses have used orientation markers on the stent-graft, to provide an indicator to a physician of directional placement of the stent-graft. In particular, the orientation marker allows a physician to properly understand the position of a portion of the prosthesis, and in the case of misalignment the physician may use the orientation marker to rotationally correct the alignment of the prosthesis.

While use of an orientation marker provides various benefits, an orientation marker may be difficult to visualize under certain circumstances, and may impact the profile of the delivery system.

SUMMARY

The present embodiments provide systems and methods for deploying an endoluminal prosthesis. In one example, the system comprises a sheath, and a stent-graft disposed within the sheath in a delivery state. A pusher having proximal and distal sections is disposed at least partially within the sheath in the delivery state. An orientation marker is disposed on the pusher. The orientation marker extends less than 360 degrees around a circumference of the pusher.

In one embodiment, the proximal section of the pusher comprises a smaller diameter relative to the distal section of the pusher, and the orientation marker is disposed on the proximal section of the pusher. Optionally, the orientation marker may be embedded into an outer surface of the pusher, or may be disposed on a band that is disposed over the proximal section of the pusher.

In one example, the stent-graft is bifurcated and comprises a main body, plus ipsilateral and contralateral limbs, and the orientation marker is positioned in a direction facing the contralateral limb in the delivery state. In one example, the contralateral limb comprises a distal end having a radiopaque ring, and the orientation marker may be oriented in a radially inward direction towards the radiopaque ring on the contralateral limb.

The proximal section of the pusher may be disposed within the ipsilateral limb, and a proximal end of the pusher may be disposed at a location distal to a distal end of the contralateral limb. Further, the orientation marker may be positioned between spaced-apart stents of the ipsilateral limb, such that the orientation marker lacks an overlap with the stents of the ipsilateral limb in the delivery state.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIGS. 1-2 are, respectively, front and side views of a first embodiment of a system for deploying an endoluminal prosthesis, with a pusher that is disposed within a sheath and distal region of an ipsilateral limb being shown in solid lines for illustrate purposes.

FIGS. 3-4 are, respectively, side and front views illustrating features of the pusher and orientation marker of the system of FIGS. 1-2.

FIGS. 5-6 are, respectively, side and front views illustrating features of an alternative orientation marker.

FIGS. 7-8 are, respectively, side and front views illustrating features of a further alternative orientation marker.

DETAILED DESCRIPTION OF THE PREFERRED EMBODIMENTS

In the present application, the term "proximal" refers to a direction that is generally closest to the heart during a medical procedure, while the term "distal" refers to a direction that is furthest from the heart during a medical procedure.

The embodiments described below are in connection with systems and methods for the introduction and deployment of an implantable medical device in a vessel, such as endovascular prostheses, but could also be used for deploying a range of implantable medical devices including, but not limited to, stents, occlusion devices and the like.

Referring to FIGS. 1-2, an example of a system 10 for deploying an endoluminal prosthesis comprises a stent-graft 20 including a main body 30 having proximal and distal regions 32 and 33, and a lumen 35 extending therebetween. In this example, the stent-graft 20 is bifurcated such that the distal region 33 of the main body 30 transitions into ipsilateral and contralateral limbs 40 and 50, respectively.

The ipsilateral limb 40 comprises proximal and distal ends 42 and 43 and a lumen 45 extending therebetween, while the contralateral limb 50 similarly comprises proximal and distal ends 52 and 53 and a lumen 55 extending therebetween. The lumens 45 and 55 of the ipsilateral and contralateral limbs 40 and 50, respectively, are each in fluid communication with the lumen 35 of the main body 30.

The exemplary stent-graft 20 is suitable for treating an array of medical conditions, and may be especially suited for treating an abdominal aortic aneurysm at or slightly above the aortic bifurcation. As will be appreciated, the main body 30 may be positioned in the abdominal aorta slightly above the aortic bifurcation, while the ipsilateral limb 40 may extend into one external iliac artery and the contralateral limb 50 may extend into, or be positioned slightly above, the opposing external iliac artery. The contralateral limb 50 may be shorter in length than the ipsilateral limb 40, as depicted in FIGS. 1-2.

Various modular components may be provided for the stent-graft 20, for example, an extension stent-graft that is configured to overlap with the distal end 53 of the contralateral limb 50. Such an extension stent-graft will have a proximal end that sealingly overlaps with the contralateral limb 50, and will have a distal end that sealingly engages an inner surface of the external iliac artery.

However, while references to treatment of an aneurysm at or near the aortic bifurcation may be explained as one example, it will be appreciated that the exemplary stent-graft 20, or modified stent-grafts, can be positioned at other bodily locations to treat aneurysms or other conditions, using the system and methods described in further detail below.

Graft material 21 of the main body 30, the ipsilateral limb 40 and the contralateral limb 50 may be made of any material known in the art. For example, the graft material 21 may be made of an expanded polytetrafluoroethylene (ePTFE), polytetrafluoroethylene, silicone, polyurethane, polyamide (nylon), as well as other flexible biocompatible materials. The graft bodies also can be made of known fabric graft materials such as woven polyester, polyetherurethanes, or polyethylene. The graft bodies also may include a bioremodelable material such as reconstituted or naturally-derived collagenous materials, extracellular matrix (ECM) material, submucosa, renal capsule membrane, dermal collagen, dura mater, pericardium, fascia lata, serosa, peritoneum or basement membrane layers, or intestinal submucosa, including small intestinal submucosa (SIS), stomach submucosa, urinary bladder submucosa, uterine submucosa, or other suitable materials.

Further, as shown in FIGS. 1-2, the main body 30, the ipsilateral limb 40 and the contralateral limb 50 may comprise at least one support structure 36, such as a stent. The support structure 36 may include a single, unitary structure or a plurality of independent structures. The support structure 36 and/or various portions thereof may be disposed on the inner surface and/or outer surface of the graft body 21. Multiple support structures 36 may be positioned at any points along a length of the stent-graft 20, as generally depicted in FIGS. 1-2.

The support structure 36 of the stent-graft 20 may have any suitable stent pattern known in the art. One example of a stent pattern is the Z-stent or Gianturco stent design. Each Z-stent may include a series of substantially straight segments or struts interconnected by a series of bent segments or bends. The bent segments may include acute bends or apices. The Z-stents are arranged in a zigzag configuration in which the straight segments are set at angles relative to one another and are connected by the bent segments. Alternative stents may include, for example, annular or helical stents. The stents mentioned herein may be made from standard medical grade stainless steel. Other stents may be made from nitinol or other shape-memory materials.

In the current, non-limiting example, a plurality of Z-stents 36a are disposed external to the graft material 21 at spaced-apart locations along the main body 30, the ipsilateral limb 40 and the contralateral limb 50. An internal Z-stent 36b is disposed along the proximal region 32 of the main body 30, as shown in FIGS. 1-2.

Further, an attachment stent 37 may be provided, having a distal end attached to the proximal region 32 of the main body 30, and a proximal end that extends proximally beyond the graft material 21, as shown in FIGS. 1-2. If the graft material 21 of the main body 30 is disposed within the abdominal aorta above an aortic bifurcation, then the attachment stent 37 may span the renal arteries, whereby blood may flow through the struts of the attachment stent 37 and into the renal arteries since the graft material 21 is not present at this location. It is noted that the attachment stent 37 is shown in a partially deployed state in FIGS. 1-2.

The system 10 further comprises a cannula 60 and an atraumatic tip 65, which may be used as part of a deployment device. The cannula 60 comprises a tubular member having proximal and distal regions, and a lumen extending between the proximal and distal regions. The lumen of the cannula 60 is sized to allow the cannula 60 to be advanced over a wire guide.

The atraumatic tip 65 may be affixed to an exterior surface along the proximal region of the cannula 60, using a suitable adhesive or mechanical attachment mechanism. The atraumatic tip 65 may be formed from an atraumatic material, which comprises proximal and distal ends 66 and 67, respectively, with a taper disposed therebetween. The attachment stent 37 of the stent-graft 20 may be secured to the cannula 60 by a retention arrangement immediately distal of the atraumatic tip 65, as explained further below.

The system 10 further comprises a pusher 70, which is disposed coaxially over a section of the cannula 60. The pusher 70 comprises a proximal end 72, a distal end that extends outside of the body, and a lumen 75 (best seen in FIG. 3) extending therebetween. A proximal section 72a of the pusher 70 comprises a reduced diameter, relative to a distal section 73a of the pusher 70. A taper 74 is disposed between the proximal and distal sections 72a and 73a of the pusher 70 to achieve the diameter change between sections, as shown in FIGS. 1-8.

In some embodiments, the pusher 70 may comprise a lumen 79 for housing at least one trigger wire 95, as depicted in FIGS. 3-4 (it is noted that the trigger wire 95 is not depicted in FIGS. 1-2 for illustrative purposes). The trigger wire 95, in this example, may extend external to the pusher 70 beginning at the taper 74, and may be used to restrain one or more areas of the ipsilateral limb 40 or the distal region 33 of the main body 30. An outer diameter of collective components along the proximal section 72a of the pusher 70 is affected based on the required size of the cannula 60, which houses a desired wire guide therein, plus an outer diameter of the trigger wire 95 (i.e., after it has exited the lumen 79 near the taper 74). Optionally, the trigger wire 95 may extend proximally beyond the proximal end 72 of the pusher 70, and in some embodiments the proximal end 72 or proximal section 72a may comprise a notch to receive and guide a portion of the trigger wire 95 externally of the pusher 70.

An orientation marker 80 is disposed on the pusher 70, at or near the proximal end 72. The orientation marker 80 preferably is attached to the proximal section 72a of the pusher 70, in a manner that does not increase the profile of the pusher 70 radially outward further than a diameter of the distal section 73a. In some embodiments, the orientation marker 80 may be embedded into an outer surface 76 at the proximal region 72a of the pusher 70, thereby not increasing the outer diameter along the proximal region 72a, as best seen in FIG. 4 and FIG. 6, below.

In one embodiment, the orientation marker 80 faces in a direction towards the contralateral limb 50. The orientation marker 80 allows a physician to properly understand the position of the "contralateral gate," i.e., the opening at the distal end 53 of the contralateral limb 50, as will be described in further detail below.

The orientation marker 80 comprises a radiopaque material, which is visible to a physician during the procedure. In one example, the orientation marker 80 comprises a gold marker, although other materials may be used. If one embodiment, the primary material of the pusher 70 itself may does comprise a radiopaque material, in order to facilitate visualization of the orientation marker 80.

A sheath 90 houses other components of the system 10 during delivery. In an initial delivery state, the sheath 90 extends proximally to the atraumatic tip 65 and covers the stent-graft 20, thus securing the stent-graft 20 in a reduced diameter delivery profile. As illustrated in FIGS. 1-2, however, the sheath 90 is withdrawn distally beyond the main body 30 and each of the ipsilateral and contralateral limbs 40 and 50, so that the stent-graft 20 is exposed in a partially deployed state.

In one exemplary method of use, a guide wire is inserted into a patient's vasculature towards a target site. Then, the atraumatic tip 65, cannula 60, pusher 70 and stent-graft 20 are advanced over the guide wire to the target site. The delivery device is preferably "pre-loaded," such that before the delivery device is introduced into the patient's vasculature, it is pre-assembled with mechanisms that facilitate stent-graft delivery and deployment already arranged thereon. The delivery and deployment mechanisms may include, for example, one or more guide wires, catheters, sheaths, stent-grafts and combinations thereof, which are arranged on and/or are carried by the device and which remain in place during delivery of the stent-graft 20 into a patient's vasculature. As noted above, during delivery, the sheath 90 extends proximally to the atraumatic tip 65 and covers the stent-graft 20.

Then, in a next step, as illustrated in FIGS. 1-2, the sheath 90 is withdrawn distally beyond the main body 30 and each of the ipsilateral and contralateral limbs 40 and 50, so that the stent-graft 20 is exposed. The pusher 70 is held steady during withdrawal of the sheath 90.

The main body 30 and the ipsilateral and contralateral limbs 40 and 50 may be inclined to self-expand at this time, i.e., when no longer radially constrained by the sheath 90, towards their respective expanded states as shown in FIGS. 1-2. At this time, various parts of the stent-graft 20 may still be restrained by one or more retention arrangements. For example, the proximal end of the attachment stent 37 may remain secured to the cannula 60 immediately distal of the atraumatic tip 65, as depicted in FIGS. 1-2, using one or more retention arrangements. The distal region 33 of the main body 30, or the ipsilateral and contralateral limbs 40 and 50, may also be retained by another retention arrangement. Retention may be by various mechanisms, including but not limited to loops or stitches of suture material which are engaged with a trigger wire extending from an aperture (not shown) in the cannula 60, or from an aperture of the pusher 70 (as depicted in FIGS. 3-4). However, it is also contemplated that other types and methods of proximal and/or distal restraint may be used including various diameter reducing ties, fasteners or the like that are suitable for removably securing the stent-graft 20. The retaining mechanisms may be placed in any suitable arrangement or location so that the stent-graft 20 is removably secured to the delivery components.

In the partially deployed state of the stent-graft 20 shown in FIGS. 1-2, as well as the delivery state when the stent-graft 20 is entirely constrained within the sheath 90, the pusher 70 is positioned within the ipsilateral limb 40 such that the proximal end 72 of the pusher is positioned just distal to the distal end 53 of the contralateral limb 50. In this manner, there is a slight offset between the pusher 70 and the contralateral limb 50.

Advantageously, the delivery profile of the system 10 may be reduced since an overlap of components is reduced. In particular, while the proximal end 72 of the pusher 70 overlaps with the ipsilateral limb 40, and the ipsilateral and contralateral limbs 40 and 50 overlap with one another along a portion of their lengths, the pusher 70 lacks an overlap with the contralateral limb 50 such that all three parts are not overlapping in a delivery state.

Since the pusher 70 lacks an overlap with the contralateral limb 50, and because the orientation marker 80 is attached to the pusher 70, then the orientation marker 80 is also disposed just distal to the contralateral limb 50. However, the orientation marker 80 remains in close axial proximity to the distal end 53 of the contralateral limb 50, for example, within a few millimeters, and therefore provides a level of guidance on the axial positioning of the distal end 53 of the contralateral limb 50.

The orientation marker 80 extends less than 360 degrees around a circumference of the pusher 70, and faces in a circumferential direction towards the contralateral limb 50. In other words, the orientation marker 80 is positioned at a discrete circumferential position around the proximal region 72a of the pusher 70, and the circumferential portion of the pusher 70 comprising the orientation marker 80 faces the contralateral limb 50, as shown in FIG. 1. Since the orientation marker 80 comprises a radiopaque material, which is visible to a physician during the procedure, the orientation marker 80 provides a valuable indicator to the physician of directional placement of the stent-graft 20, particularly the contralateral limb 50. In particular, the orientation marker 80 allows a physician to properly understand the position of the "contralateral gate," i.e., the opening at the distal end 53 of the contralateral limb 50, and in the case of misalignment the physician may use orientation marker 80 to rotationally correct the alignment of the "contralateral gate."

Since the orientation marker 80 primarily helps with alignment of the opening at the distal end 53 of the contralateral limb 50 during delivery and deployment, there is no firm need to maintain the orientation marker 80 inside the body after these steps. The present embodiments advantageously place the orientation marker 80 on the pusher 70, which is removed after deployment of the stent-graft, since the orientation marker 80 is no longer needed after correct placement.

As a further advantage, the placement of the orientation marker 80 on the proximal region 72a of the pusher 70 facilitates delivery of a stent-graft 20 manufactured with its own markers placed at any desired location, i.e., without the orientation marker 80 on the pusher 70 interfering with markers on the stent-graft itself. As one example, the stent-graft 20 may comprise a radiopaque ring 56 at the distal end 53 of the contralateral limb 50, as shown in FIGS. 1-2. The radiopaque ring 56, positioned exactly at the opening into the contralateral limb 50, may provide a better cannulation target than the previous markers, e.g., positioned on stent struts of the contralateral limb 50. Due to visualization and spacing logistics, prior orientation markers that were coupled to the contralateral limb 50 itself, axially near the distal end 53, cannot easily remain in use with the radiopaque ring 56 at the distal end 53. More specifically, the presence of the radiopaque ring 56 (which has been found to significantly enhance cannulation of the contralateral limb), combined with an orientation marker (such as a check-mark shape) in close proximity to the radiopaque ring 56 on the contralateral limb 50 itself, has been found to render the orientation marker difficult to view. If the orientation marker is moved proximally along the stent-graft (e.g., closer to the bifurcation) in an attempt to gain more distinctive visibility (further from the radiopaque ring 56 at the contralateral gate), then either the orientation marker must overlap with a stent strut, or a gap between stent struts must be created to accommodate an orientation marker placement. However, if the orientation marker overlaps with a stent strut further above the contralateral gate, then the delivery profile is increased due to duplicity of materials. Further, if a gap is created between stent struts closer to the bifurcation to accommodate an orientation marker placement, then the structural integrity of the stent-graft may be weakened by having further spaced-apart stent struts at the important bifurcation location, where it may be particularly desirable to have struts in close proximity.

In the present embodiments, the orientation marker 80 has been moved off the contralateral limb (and the stent-graft altogether) and onto the pusher 70 and points inward towards the contralateral limb 50 to provide guidance. By moving the orientation marker 80 to the pusher 70, it is not placed over any struts of the stent-graft 20, thereby reducing delivery profile. The orientation marker 80 on the pusher 70 only overlaps with the ipsilateral limb 40, and may be spaced between stent struts of the ipsilateral limb 40, such that the orientation marker lacks an overlap with the stents of the ipsilateral limb 40 in the delivery state, as depicted in FIGS. 1-2. If a greater spacing is needed between stent struts of the stent-graft 20 to accommodate the orientation marker 80 without axially overlapping stent struts, it may be advantageous to provide greater spacing among the stents along the ipsilateral limb 40 a distance away from the bifurcation, as compared to stent struts of the stent-graft 20 closer to bifurcation.

After the orientation marker 80 facilitates guidance of a device, such as a wire guide, that cannulates the contralateral limb 50, the retention structure that secures the attachment stent 70 to the cannula 60 may be released to allow full expansion of the attachment stent 70. A delivery system advanced over the wire guide that has cannulated the contralateral limb 50 then may deploy a different stent-graft that spans between the contralateral limb 50 and the external iliac artery. Any remaining retention structures are released to fully deploy the ipsilateral limb 40 and the remainder of the stent-graft 30.

Referring to FIGS. 3-8, various different orientation marker arrangements are shown. In the embodiment of FIGS. 3-4, a generally "C-shaped" orientation marker 80 is provided. In the embodiment of FIGS. 5-6, an alternative "checkmark-shaped" orientation marker 80' is provided. In either of the embodiments of FIGS. 3-6, the markers 80 and 80' may be embedded into an outer surface 76 at the proximal region 72a of the pusher 70, and then adhered to the pusher 70. While "C-shaped" and "checkmark-shaped" orientation markers have been depicted, it will be appreciated that various other configurations may be used.

In FIGS. 7-8, an alternative orientation marker 80" is secured to, or embedded into, a separate band 82, which in turn is disposed over the narrow proximal region 72a of the pusher 70. In the embodiment of FIGS. 7-8, the band 82 may comprise elastic characteristics to assume a friction fit around the pusher 70, and/or may be adhered or mechanically secured to the pusher 70. It is noted that, while a trigger wire 95 is only depicted in the embodiment of FIGS. 3-4, such a trigger wire may also be included in the embodiments of FIGS. 5-6 and FIGS. 7-8.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. A system for deploying an endoluminal prosthesis, the system comprising:
   an atraumatic tip;
   a sheath;
   a stent-graft disposed within the sheath in a delivery state;
   a pusher having proximal and distal sections, wherein the proximal section of the pusher is closer to the atraumatic tip than the distal section, and wherein the pusher is disposed at least partially within the sheath in the delivery state; and
   an orientation marker disposed on the pusher,
   wherein the stent-graft is bifurcated and comprises a main body, plus ipsilateral and contralateral limbs,
   wherein in the delivery state, the proximal section of the pusher is disposed within the ipsilateral limb, wherein a proximal end of the pusher is disposed at a location distal to a distal end of the contralateral limb.

2. The system of claim 1, wherein the proximal section of the pusher comprises a smaller diameter relative to the distal section of the pusher, wherein the orientation marker is disposed on the proximal section of the pusher.

3. The system of claim 1, wherein the orientation marker is embedded into an outer surface of the pusher.

4. The system of claim 1, wherein the orientation marker is disposed on a band that is disposed over the proximal section of the pusher, wherein the proximal section of the pusher comprises a smaller diameter relative to the distal section of the pusher.

5. The system of claim 1, wherein the orientation marker is positioned in a direction facing the contralateral limb in the delivery state.

6. The system of claim 5, wherein the orientation marker extends less than 360 degrees around a circumference of the pusher.

7. The system of claim 5, wherein the contralateral limb comprises a distal end having a radiopaque ring, wherein the orientation marker is oriented in a radially inward direction towards the radiopaque ring on the contralateral limb.

8. The system of claim 1, wherein the orientation marker is positioned between spaced-apart stents of the ipsilateral limb, such that the orientation marker lacks an overlap with the stents of the ipsilateral limb in the delivery state.

9. The system of claim 1 further comprising a cannula, wherein the atraumatic tip is coupled to a proximal region of the cannula, wherein the pusher is slidably disposed over the cannula.

* * * * *